United States Patent
Shah et al.

(10) Patent No.: US 10,675,246 B2
(45) Date of Patent: Jun. 9, 2020

(54) ORALLY ADMINISTRABLE COMPOSITIONS COMPRISING CALCIUM

(71) Applicant: Cerolife LLC, Valley Cottage, NY (US)

(72) Inventors: Manish S. Shah, West Caldwell, NJ (US); Ray J. DiFalco, Ridgewood, NJ (US)

(73) Assignee: CEROLIFE LLC, Valley Cottage, NY (US)

( * ) Notice: Subject to any disclaimer, the term of this patent is extended or adjusted under 35 U.S.C. 154(b) by 0 days.

(21) Appl. No.: 14/777,287

(22) PCT Filed: Mar. 15, 2014

(86) PCT No.: PCT/US2014/029941
§ 371 (c)(1),
(2) Date: Sep. 15, 2015

(87) PCT Pub. No.: WO2014/145219
PCT Pub. Date: Sep. 18, 2014

(65) Prior Publication Data
US 2016/0022586 A1    Jan. 28, 2016

Related U.S. Application Data

(60) Provisional application No. 61/798,689, filed on Mar. 15, 2013.

(51) Int. Cl.
*A61K 9/24* (2006.01)
*A61K 33/06* (2006.01)
*A61K 33/10* (2006.01)

(52) U.S. Cl.
CPC ............. *A61K 9/209* (2013.01); *A61K 33/06* (2013.01); *A61K 33/10* (2013.01)

(58) Field of Classification Search
CPC ...... A61K 9/2027; A61K 33/06; A61K 33/10; A61K 2300/00
USPC .................................................. 424/464, 687
See application file for complete search history.

(56) References Cited

U.S. PATENT DOCUMENTS

| 5,879,698 A | 3/1999 | Ellenbogen et al. |
| 2007/0128272 A1 | 6/2007 | Zerbe et al. |
| 2011/0064816 A1 | 3/2011 | Alagumurugan et al. |
| 2011/0159093 A1 | 6/2011 | Sheth et al. |
| 2012/0244218 A1* | 9/2012 | Durkee ............... A61K 9/2054 424/457 |

FOREIGN PATENT DOCUMENTS

| EP | 1 591 143 A1 | 11/2005 |
| WO | WO 2012/134590 A2 | 10/2012 |

OTHER PUBLICATIONS

Shiyani et al.; title: Formulation and Evaluation of Bi-layer Tablet of Metoclopramide Hydrochloride and Ibuprofen; AAPS PharmSciTech, vol. 9, No. 3, pp. 818-892, published online Jul. 9, 2008.*
Author: Allen Bethea; title: The Difference between Citracal & Caltrate; Last Updated: Jun. 16, 2015 Downloaded from http://www.livestrong.com/article/519569-the-difference-between-citracal-caltrate/.*
Authors: Rohan D. Deshpande, et al; Title: Bi-Layer Tablets—An Emerging Trend: A Review Published: Oct. 1, 2011.*
author unknown, title: CITRACAL Caplets + D, downloaded from drugs.com on Nov. 6, 2017.*
Goss, et al.; title: Determination of calcium salt solubility with changes in pH and P(CO(2)), simulating varying gastrointestinal environments; J Pharm Pharmacol. Nov. 2007;59(11):1485-92.*
International Search Report of PCT/US2014/029941 dated Jul. 24, 2014.
Patel et al., "A Review on Bilayer Tablets," Journal of Drug Discovery and Therapeutics. vol. 1(3). 2013. pp. 40-48.
Supplementary European Search Report issued is European Patent Application No. 14764664.0 dated Oct. 20, 2016.

* cited by examiner

*Primary Examiner* — Yanzhi Zhang
(74) *Attorney, Agent, or Firm* — IP Pundit LLC

(57) ABSTRACT

Orally administrable compositions comprising calcium, methods of administration, and methods of making the same.

11 Claims, 2 Drawing Sheets

ORALLY ADMINISTRABLE COMPOSITIONS COMPRISING CALCIUM

CROSS REFERENCE TO RELATED APPLICATION(S)

This application is a National Stage entry of International Application No. PCT/US2014/029941, filed on Mar. 15, 2014, which claims priority to U.S. Provisional Patent Application No. 61/798,689, filed on Mar. 15, 2013, each of which is incorporated herein by reference in its entirety.

FIELD OF THE INVENTION

The present invention provides orally administrable compositions comprising calcium, methods of administration, and methods of making the same.

BACKGROUND OF THE INVENTION

Calcium plays an important role in many bodily functions, including nerve transmission, muscle contraction, pancreatic insulin release, intracellular signaling, hormone secretion, and hydrogen ion release from the stomach. Calcium is also a cofactor for some enzyme reactions and in blood coagulation. In addition, the body stores calcium in the bones and teeth and contributes to their structural integrity and function. Normal values of total calcium for humans range from about 8.8 to 10.3 mg/dL or 2.20 to 2.56 mmol/L. In adults, the total calcium content is 20 to 25 g/kg of fat-free tissue, and about 44% of this calcium is in skeletal tissue. Approximately 1% of skeletal calcium is freely exchangeable with that of the extracellular fluid. The reservoir of calcium in the bones maintains the concentration of calcium in the plasma constantly. About 40% of the calcium in the extracellular fluid is bound to plasma proteins such as albumin, about 5 to 15% is complexed with phosphate and citrate, and about 45 to 44% is in unbound, unionized form. Calcium is absorbed primarily in the duodenum as a result of the presence of active absorption sites in the upper GI tract.

Bones undergo continuous remodeling, with constant resorption and deposition of calcium into new bone. As humans age, the balance between bone resorption and deposition changes, and bone breakdown begins to exceed bone formation. The resulting bone loss can increase the risk of osteoporosis, especially in postmenopausal women. Adequate calcium intake, both through diet and with supplements, is important for both preventing and treating osteoporosis, osteomalacia, and other calcium-related conditions. In addition, some studies indicate that calcium intake may be associated with a reduced risk of colon cancer and a blood pressure-lowering effect.

Calcium supplements are widely administered to supplement dietary intake of calcium. However, the development of effective orally administrable calcium compositions has been hindered by a number of factors, including gastric emptying time, the variation in pH in different segments of the gastrointestinal tract, and the difficulty in localizing an oral delivery system in a selected region of the gastrointestinal tract. The bioavailability of calcium from different preparations sometimes varies, as often the manufacturing process has an effect on bioavailability. For most commercially available products, which are typically immediate-release formulations, bioavailability is generally low, and calcium absorption in adults is thought to average about 25-35% of the available calcium in the dosage form. Therefore, subjects taking calcium supplements often receive less than optimal amounts of calcium. With administration of currently available formulations, which are mostly immediate-release formulations, subjects often experience both hypercalcemia and hypocalcemia. Hypercalcemia refers to an excessive amount of calcium in the blood, and symptoms associated with hypercalcemia include nausea, vomiting, and calcium deposition in the heart and kidneys. Hypocalcemia refers to low levels of calcium in the blood, and symptoms associated with hypocalcemia include tingling, numbness, and muscle twitches. In severe cases, tetany, or muscle spasms, may occur. Subjects taking commercially available immediate release formulations, which typically contain high amounts of calcium, can experience hypercalcemia at first, then because the body is unable to absorb all of the elemental calcium at once, undissolved forms of calcium remain in the gastrointestinal (GI) tract. Between doses, subjects can sometimes experience hypocalcemia, as they are not receiving adequate amounts of calcium, and gastric side effects may be experienced due to the presence of undissolved calcium in the GI tract. There are difficulties in producing effective immediate-release formulations of calcium, as often a very large amount of elemental calcium must be present in the formulation. A currently marketed extended release formulation combines calcium carbonate and calcium citrate in one matrix/portion. It is designed to deliver calcium as a slow, sustained release profile with no immediate release component. This formulation also does not provide effective calcium supplementation, as initially, calcium is delivered very slowly (and in inadequate amounts, resulting in hypoglycemia) and there is inadequate absorption. In addition, undissolved calcium carbonate is present in the lower GI tract, and the high pH of the GI tract makes the calcium carbonate insoluble. The high incidence of gastric side effects creates a compliance issue for patients, and the severity of the side effects often results in patients skipping doses or discontinuing therapy all together.

There is a need in the art for orally administrable calcium compositions with good bioavailability which provide an effective amount of calcium to subjects with decreasing gastric side effects. The present invention addresses this need in the art by providing calcium compositions which provide improved bioavailability and absorption. The present invention also provides compositions which provide biphasic, controlled release of calcium. This type of release may enhance bioavailability and absorption by providing calcium in small continuous amounts, avoiding effects such as hypocalcemia. A first phase of release, such as immediate release of a calcium compound such as calcium carbonate, may be released immediately and absorbed mostly or fully in acidic media. A second phase of release, such an extended release of a calcium compound, such as calcium citrate, may be released. The benefits of the present invention include increased patient compliance, a higher amount of absorption of calcium with a lower dose required per dosage form, and reduced toxicity.

SUMMARY OF THE INVENTION

The present invention provides an orally administrable pharmaceutical composition comprising: a first portion comprising a calcium compound and one or more pharmaceutically acceptable excipients, wherein the first portion is formulated for immediate release, and a second portion comprising the same and/or a different calcium compound and one or more pharmaceutically acceptable excipients, wherein the second portion is formulated for extended release.

The present invention also provides methods of making an orally administrable pharmaceutical composition comprising: forming a first portion comprising a calcium compound and one or more pharmaceutically acceptable ingredients, wherein the first portion is formulated for immediate release, and applying thereto a second portion comprising a calcium compound and one or more pharmaceutically acceptable ingredients, wherein the second portion is formulated for extended release.

The present invention also provides methods of preventing, treating, or reducing the symptoms associated with a condition, comprising administering to a subject in need thereof an orally administrable composition comprising: a first portion comprising a calcium compound and one or more pharmaceutically acceptable ingredients, wherein the first portion is formulated for immediate release, and a second portion comprising the same and/or a different calcium compound and one or more pharmaceutically acceptable ingredients, wherein the second portion is formulated for extended release.

DETAILED DESCRIPTION OF THE INVENTION

Figure 1:
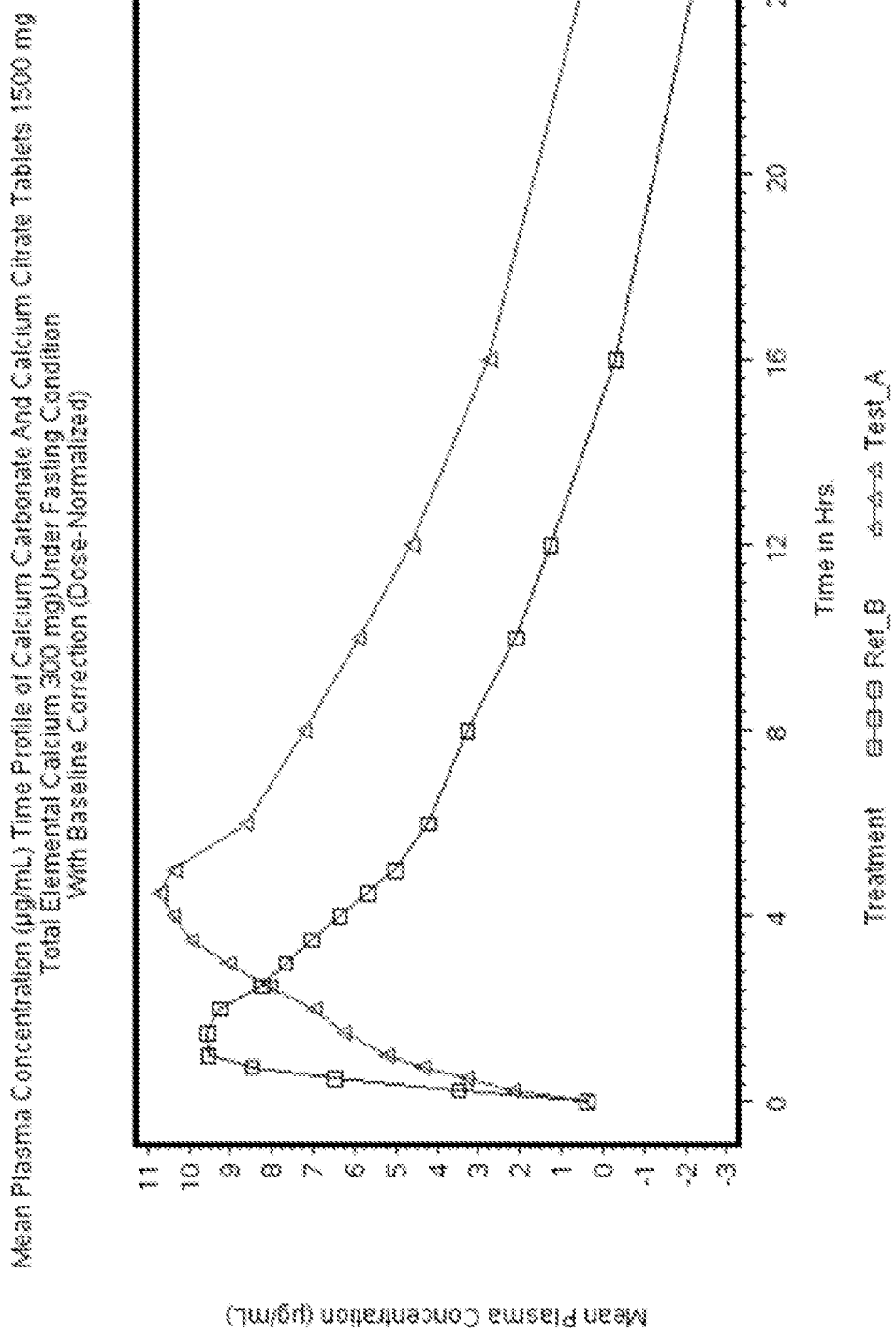
FIG. 1 shows the mean plasma concentration time profile (dose-normalized graph) relating to the experiment described in Example 3.

The present invention provides an orally administrable pharmaceutical composition comprising: a first portion comprising a calcium compound and one or more pharmaceutically acceptable excipients, wherein the first portion is formulated for immediate release, and a second portion comprising the same and/or a different calcium compound and one or more pharmaceutically acceptable excipients, wherein the second portion is formulated for extended release. In preferred embodiments, the composition comprises a tablet or capsule, preferably a tablet.

The term "calcium compound" refers to any compound containing calcium, including but not limited to calcium acid derivatives, such as calcium acid salts and esters. Examples of calcium acid derivatives include, but are not limited to, calcium carbonate, calcium citrate, calcium citrate malate, calcium lactate, calcium phosphate, and calcium gluconate. The orally administrable composition of the present invention may comprise one or more calcium compounds. The first portion and second portion each comprise at least one calcium compound, and in some embodiments, either or both of the first portion and second portion may comprise more than one calcium compound. In some embodiments, the first portion contains exactly one calcium compound, preferably calcium carbonate. In some embodiments, the first portion contains exactly two calcium compounds, preferably calcium carbonate and calcium citrate. The second portion may comprises one or more calcium compounds, and the one or more calcium compounds in the second portion may be the same or different than the calcium compound(s) in the first portion. In some preferred embodiments, the second portion contains exactly one calcium compound, preferably calcium citrate. In some embodiments, the total amount of calcium compound(s) in the orally administrable composition is about 50 mg to 2,500 mg, preferably about 250 mg to about 2,000 mg, more preferably about 500 mg to 1,750 mg, even more preferably about 750 mg to 1,500 mg, and most preferably about 1,000 mg to 1,250 mg. In some embodiments, the total amount of elemental calcium in the orally administrable composition is about 25 mg to 1,000 mg, preferably about 50 mg to 750 mg, more preferably about 100 mg to 500 mg, and most preferably about 200 mg to 300 mg.

In some embodiments, the first portion comprises about 100 mg to 1,000 mg, preferably about 250 mg to about 750 mg, more preferably about 400 mg to 600 mg of calcium compound. In some embodiments, the first portion comprises about 100 mg to 500 mg, preferably about 200 mg to 300 mg, and most preferably about 250 mg of calcium citrate, and further comprises about 100 mg to 500 mg, preferably about 200 mg to 300 mg, and most preferably about 250 mg of calcium carbonate.

In some embodiments, the second portion comprises 100 mg to 2,000 mg, preferably about 250 mg to about 1,500 mg, more preferably about 500 mg to 100 mg, and most preferably about 700 mg to 800 mg of calcium compound. In some embodiments, the second portion comprises 100 mg to 2,000 mg, preferably about 250 mg to about 1,500 mg, more preferably about 500 mg to 1,000 mg, even more preferably about 700 mg to 800 mg, and most preferably about 750 mg of calcium citrate.

In some embodiments, the second portion may comprise about 25% to 90%, preferably about 50% to 75%, of the total amount of calcium compound(s) in the composition.

The term "portion" refers to a section or part of the orally administrable composition. The first portion and second portion of the orally administrable composition generally refer to separate sections or parts of the composition. In some embodiments, part or all of the first portion may be in direct physical contact with part or all of the second portion. A part is in "direct physical contact" with another part when the parts are directly adjacent to each other in the pharmaceutical composition without intervening or intermediate portion. In some embodiments, the first portion and second portion are not in direct physical contact with each other, and no part of the first portion is in direct physical contact with the second portion in the pharmaceutical composition. For example, a further portion, such as one or more intermediate layers, may be present between the first portion and the second portion.

In some embodiments wherein the first portion is in direct physical contact with the second portion, substantially all or all of the entire surface area of the second portion may be in contact with the first portion, such as when the second portion comprises an inner layer or core which is substantially or completely surrounded by the first portion (for example, a layer or coating), or when there are multiple second portion sections which are distributed within the first portion. In some embodiments, only part of the surface area (less than the entire surface area) of the first portion and second portion are in contact with each other in the composition. In some embodiments, about 10% to 90%, preferably about 25% to 75%, more preferably about 35% to 65%, and most preferably about 40% to 60% of the surface area of the first portion is in physical contact with the second portion in the pharmaceutical composition.

In some embodiments, the first portion and second portion are each layers, and the first portion and second portion may together form a layered tablet, such as a bilayer tablet. In some embodiments wherein the first portion and second portion form a bilayer tablet, only part of the surface area of each of the two layers may be in direct physical contact with each other in the tablet. For example, the first portion and second portion may form a side-by-side arrangement, wherein less than the entire surface area (for example, one side) of the first portion layer physically contacts one side of the second portion layer in the composition.

In some embodiments wherein the pharmaceutical composition comprises additional portions such as layers, the pharmaceutical composition may comprise a multilayer tablet. In some embodiments wherein the composition comprises a multilayer tablet, one or more additional layers may be present between the first portion layer and the second portion layer as intermediate layers, and/or outside of the first portion layer and second portion layer.

In some embodiments, the composition may comprise a first portion core surrounded fully or partially by a second portion layer. In some embodiments, one of the portions may be present within the other portion. For example, the composition may comprise a single first portion and multiple second portions, wherein the multiple second portions are discrete areas which are distributed within the first portion.

The term "immediate release" is used to refer to a composition which is formulated to release about 80% or more of an active ingredient after 4 hours, more preferably after 2 hours, and most preferably after 1 hour.

The term "extended release" is used to refer to a composition which is formulated to provide for the delayed and/or gradual release of an active ingredient after and/or over an extended period of time, preferably over 2 to 48 hours, more preferably over 4 to 36 hours, and most preferably over 6 to 24 hours. The term "extended release" includes controlled release and delayed release. A second portion, which is formulated for extended release, may be accomplished in a number of ways, for example, by embedding the calcium compound in a substance that the body is slow to dissolve, such that the active ingredient slowly and gradually releases from the substance, by embedding the calcium compound in a substance that allows for the calcium compound to slowly diffuse out, or by releasing the calcium compound in one or more boluses (i.e., bursts) separated by a delay. In some embodiments of the present invention, in the second portion, preferably <25%, more preferably <20%, of the total amount of calcium compound(s) is released in the first hour; preferably 15-50%, more preferably 20-45%, of the total amount of calcium compound(s) is released in the first two (2) hours; preferably 40-80%, more preferably 45-75%, of the total amount of calcium compound(s) is released in the first four (4) hours; and preferably >75%, more preferably >80%, of the total amount of calcium compound(s) is released after eight (8) hours. In some embodiments of the present invention in the present invention, in the second portion, preferably about 5% to about 25% of the drug is released after 1 hour, from about 40% to about 75% of the drug is released after 8 hours, and not less than about 80% is released after 18 hours. In some alternative embodiments of the present invention containing an extended release portion, preferably about 10% to about 30% of the drug is released after 2 hours, from about 40% to about 70% of the drug is released after 8 hours, and at least about 80% of the drug is released after 22 hours.

In some embodiments, the second portion of the composition may comprise one or more polymers which allow for the extended release of the calcium compound. In some embodiments, the one or more polymers comprise hydrophilic polymers. Hydrophilic polymers useful herein include, but are not limited to: polyalkylene oxides, particularly poly(ethylene oxide), polyethylene glycol and poly (ethylene oxide)-poly(propylene oxide) copolymers; cellulose derivatives such as cellulose ethers, alkylcelluloses, hydroxyalkylcelluloses, hydroxyalkylalkylcelluloses, e.g. methylcellulose, hydroxymethylcellulose, hydroxyethylcellulose, hydroxypropylcellulose, hydroxybutylcellulose, hydroxyethylmethylcellulose, hydroxypropylmethylcellulose; carboxyalkylcelluloses, carboxyalkylalkylcelluloses, carboxyalkylcellulose esters, e.g. carboxymethylcellulose and its alkali metal salts; acrylic acid and methacrylic acid polymers, copolymers and esters thereof, preferably formed from acrylic acid, methacrylic acid, methyl acrylate, ethyl acrylate, methyl methacrylate, ethyl methacrylate, and copolymers thereof, with each other or with additional acrylate species such as aminoethyl acrylate; maleic anhydride copolymers; polymaleic acid; poly(acrylamides) such as polyacrylamide per se, poly(methacrylamide), poly(dimethylacrylamide), and poly(N-isopropyl-acrylamide); poly (olefinic alcohol) such as poly(vinyl alcohol); poly(N-vinyl lactams) such as poly(vinyl pyrrolidone), poly(N-vinyl caprolactam), and copolymers thereof; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol and polyoxyethylated glucose; polyoxazolines, including poly(methyloxazoline) and poly(ethyloxazoline); polyvinylamines; polyvinylacetates, including polyvinylacetate per se as well as ethylene-vinyl acetate copolymers, polyvinyl acetate phthalate, and the like; polyimines, such as polyethyleneimine; starch and starch-based polymers; polyurethane hydrogels; chitosan; polysaccharide gums; zein; and shellac, ammoniated shellac, shellac-acetyl alcohol, and shellac n-butyl stearate. In some embodiments, the hydrophilic polymer comprises a polymer of acrylic acid crosslinked with allyl ethers of pentaerythritol, which is marketed under the trade name CARBOPOL® 71G NF.

The orally administrable composition may optionally also contain sustained or extended release and/or enteric coating. Examples of such materials are cellulose acetate phthalate, hydroxypropyl methylcellulose phthalate, polyvinyl acetate phthalate, methacrylic acid:acrylic ester copolymer, hydroxypropyl methylcellulose acetate succinate, shellac, cellulose acetate trimellitate, and mixtures thereof. The diffusion layer may also contain water-soluble polymers such as polyvinylpyrrolidone, hydroxypropyl cellulose, hydroxypropyl methylcellulose, polyethylene glycol having a molecular weight of from 1,700 to 20,000 and polyvinyl alcohol and monomers therefor and mixtures thereof. The use of sustained, extended and enteric coating materials is generally known in the pharmaceutical arts, and as would be understood to one skilled in the art, any suitable sustained, extended and enteric coating materials or similar agents may be used in conjunction with the present invention and embodiments thereof.

The orally administrable composition may also comprise one or more other components. Examples of other components include pharmaceutically acceptable excipients including, but are not limited to, the following: plasticizers, anti-adhesives, fillers/diluents/binders, disintegrants, glidants and lubricants, surfactants, colorants, flavoring agents, pH adjusting agents, solubilizing agents, wetting agents, solvent resistant agents and buffering agents. Other suitable pharmaceutically acceptable excipients are described in

*Remington: The Science and Practice of Pharmacy*, Lippincott Williams and Wilkins, Baltimore, Md. (1995), incorporated herein by reference.

Examples of plasticizers include, but are not limited to, triacetin, acetylated monoglyceride, olive oil, acetyl tributyl citrate, acetyl triethyl citrate, glycerin, sorbitol, polyethylene glycol, and polypropyleneglycol.

Examples of anti-adhesives include, but are not limited to, metallic stearates, microcrystalline cellulose, calcium phosphate, AEROSIL® 200, and talc. Those of ordinary skill in the art would understand the need for and applicability of such other components to overcome manufacturing, shelf-life or release profile issues.

Examples of fillers/diluents/binders include, but are not limited to, sucrose, sorbitol, mannitol, various grades of lactose, various grades of microcrystalline cellulose, dextrins, maltodextrins, starches or modified starches, sodium phosphate, calcium phosphate, calcium carbonate, gelatin, polyvinylpyrrolidone, and sodium carboxymethylcellulose.

Examples of disintegrants include, but are not limited to, cellulose derivatives, including microcrystalline cellulose, low-substituted hydroxypropyl cellulose, croscarmellose sodium, alginic acid, insoluble polyvinlypyrrolidone, and sodium carboxymethyl starch.

Examples of glidants and lubricants may be incorporated such as stearic acid, metallic stearates, talc, waxes, and glycerides with high melting temperatures, colloidal silica, sodium stearyl fumarate, polyethyleneglycols, and alkyl sulphates.

Examples of surfactants include, but are not limited to, non-ionic surfactants (such as various grades of polysorbate); anionic surfactants (such as docusate sodium and sodium lauryl sulfate), and cationic surfactants (such as benzalkonium chloride). An example of an amphoteric surfactant is 1,2-diacyl-L-phosphatidylcholine.

Other appropriate pharmaceutically acceptable excipients may include colorants, flavoring agents, pH adjusting agents, solubilizing agents, wetting agents, solvent resistant agents and buffering agents.

In some embodiments, the orally administrable composition releases at about 10% or more, more preferably about 25% or more, and most preferably about 50% or more of the total amount of calcium compound(s) in the duodenum.

The present invention also provides methods of making an orally administrable composition comprising: forming a first portion comprising a calcium compound and one or more pharmaceutically acceptable ingredients, wherein the first portion is formulated for immediate release, and applying thereto a second portion comprising a calcium compound and one or more pharmaceutically acceptable ingredients, wherein the second portion is formulated for extended release. The first portion and second portion may be formed by any methods known in the art. In embodiments wherein the composition comprises a tablet dosage form, the tablet may be formed by any methods, such as those described in *Pharmaceutical Dosage Forms: Tablets, Third Edition*, Informa Healthcare, New York, N.Y. (2010), incorporated herein by reference. In some embodiments wherein the first portion and second portion together form a layered tablet, such as a bilayer or multilayer tablet, layers may be in powder form, and the layers may be compressed together using a tablet press.

The present invention also provides methods of treating or reducing the symptoms associated with a medical condition, comprising administering to a subject in need thereof an orally administrable composition comprising: a first portion comprising a calcium compound and one or more pharmaceutically acceptable ingredients, wherein the first portion is formulated for immediate release, and a second portion comprising the same and/or a different calcium compound and one or more pharmaceutically acceptable ingredients, wherein the second portion is formulated for extended release. In some embodiments, the medical condition is a disease, disorder, illness, medical state, syndrome, or morbidity which would be improved, alleviated, treated, cured, or ameliorated by the administration of calcium. Examples of medical conditions include but are not limited to calcium deficiency (hypocalcemia) and disorders associated with calcium deficiency, such as osteoporosis, osteopenia, and rickets. Examples of medical conditions also include disorders which could be prevented or improved with administration of calcium, including but not limited to cancer (such as colorectal cancer), diabetes, obesity, and high blood pressure.

In some embodiments, the methods provide effective treatment or reduction of symptoms associated with a medical condition, while decreasing the incidence of gastric side effects typically found with calcium supplementation. This can result in improved patient compliance.

In some embodiments, the orally administrable composition of the present invention may be administered at a frequency of between 1 to 5 times daily, preferably 1 to 3 times daily, more preferably 1 or 2 times daily. The orally administrable composition may be administered with or without food. In some preferred embodiments, the orally administrable composition is administered with food, or within 3 hours, preferably within 2 hours, more preferably within 1 hour, and more preferably within 30 minutes before or after administration of food.

EXAMPLES

Example 1

The following is an example of a tablet formulation of the present invention, which comprises about 250 mg of elemental calcium. The formulation is a bilayer tablet.

| FORMULATION 1 | |
|---|---|
| Ingredient | mg/tablet |
| First portion | |
| Calcium citrate | 250.0 |
| Methocel K100M | 25.0 |
| Microcrystalline cellulose PH101 | 25.0 |
| Calcium carbonate | 250.0 |
| Magnesium stearate | 5.0 |
| Total weight of first portion | 555.0 |
| Second portion | |
| Calcium citrate | 750.0 |
| Microcrystalline cellulose | 50.0 |
| Methocel K100M | 25.0 |
| Polyethylene oxide WSR 303 | 25.0 |
| Carbomer 71G | 25.0 |
| Magnesium stearate | 10.0 |
| Total weight of second portion | 885.0 |

The formulation of Example 1 can be made by the following process:

Formulation of First Portion

1. Granulate calcium carbonate, calcium citrate, microcrystalline cellulose, and Methocel K100M, using water to density the materials. Wet mill and dry to loss on drying (LOD) of NMT 2%.

2. Mill the dried material using suitable milling equipment, screen size, and mill speed (for example, oscillating granulator #20 mesh)
3. Lubricate the milled granules by mixing the granules with magnesium stearate for 5 minutes (pass magnesium stearate through #40 mesh before adding into the granules).

Formulation of Second Portion
1. Granulate calcium citrate, microcrystalline cellulose, Methocel K100M, and polyethylene oxide, using water to densify the materials. Wet mill and dry to loss on drying (LOD) of NMT 2%.
2. Mill the dried material using suitable milling equipment, screen size, and mill speed (for example, oscillating granulator #20 mesh).
3. Add carbomer to dried granules and blend for about 15 minutes.
4. Pass the magnesium stearate through #40 mesh. Mix the dried granules with the magnesium stearate for about 5 minutes.

Formulation of Bilayer Tablet
Compress the first portion and second portion using a bilayer tablet press at the respective weight and hardness of 10 KP.

Example 2

The following experiments were conducted:

| Ingredient | Experiment 1 (Formulation 2) | Experiment 2 (Formulation 3) | Experiment 3 (Formulation 4) |
|---|---|---|---|
| Microcrystalline cellulose PH 101 | 25.0 | 25.0 | 25.0 |
| Calcium Carbonate | 400.0 | 250.0 | 250.0 |
| PVP K-30 | 10.0 | 10.0 | 10.0 |
| Magnesium Stearate | 5.0 | 5.0 | 5.0 |
| Total Part A | 440.0 | 290.0 | 290.0 |
| Calcium Citrate | 500.0 | 1000.0 | 1000.0 |
| Microcrystalline cellulose | 25.0 | 0.0 | 50.0 |
| Methocel K100M | 25.0 | 0.0 | 50.0 |
| Polyethylene Oxide WSR 303 | 25.0 | 100.0 | 50.0 |
| Carbomer 71 G | 25.0 | 0.0 | 50.0 |
| Calcium Citrate | 0.0 | 500.0 | 0.0 |
| Magnesium Stearate | 5.0 | 10.0 | 10.0 |
| Total Part B | 605.0 | 1610.0 | 1210.0 |
| Total Bi-Layer Tablet weight | 1045.0 | 1900.0 | 1500.0 |

Procedure:
Formulations 2, 3, and 4:
Part A
  Granulate Calcium carbonate, and MCC using PVP K-30 solution in water to densify the materials. Wet mill and dry to LOD of NMT 2%.
  Mill the dried material using suitable milling equipment and screen size and mill speed (Oscillating granulator #20 mesh)
  Lubricate the milled granules by mixing the granules with magnesium stearate for 5 minutes (pass magnesium stearate through #40 mesh before adding into the granules)
Formulation 3—
Part B
  Granulate Calcium Citrate (1000 mg), and PEO using water to densify the materials. Wet mill and dry to LOD of NMT 2%.
  Mill the dried material using suitable milling equipment and screen size and mill speed (Oscillating granulator #20 mesh)
  Add Carbomer into the dried granules and blend for 15 minutes
  Sift the Calcium Citrate (500 mg) and Magnesium Stearate through #40 mesh and add into the blender containing milled granules from the above step and mix for 5 minutes (pass magnesium stearate through #40 mesh before adding into the granules)
  Compress Part A and Part B using bi-layer tablet press at the respective weight and hardness of 10 KP (7-15 kp)
Formulations 2 and 4—
Part B
  Granulate Calcium Citrate, MCC, Methocel K100M and PEO using water to densify the materials. Wet mill and dry to LOD of NMT 2%.
  Mill the dried material using suitable milling equipment and screen size and mill speed (Oscillating granulator #20 mesh)
  Add Carbomer into the dried granules and blend for 15 minutes
  Sift Magnesium Stearate through #40 mesh and add into the blender containing milled granules from the above step and mix for 5 minutes.
  Compress Part A and Part B using bi-layer tablet press at the respective weight and hardness of 10 KP (7-15 kp)

The formulations from Formulations 2, 3, and 4 (Experiments 1, 2, and 3, respectively) were tested against a marketed sustained release product, CITRACAL® Calcium+Vitamin D extended release formulation ("Marketed SR"), and an immediate release (single matrix) calcium carbonate formulation ("Marketed IR"). The following table shows percent released:

TABLE 1

| Time in Hr | Marketed SR | Formulation 2 | Formulation 3 | Formulation 4 | Marketed IR |
|---|---|---|---|---|---|
| 0 | 0 | 0 | 0 | 0 | 0 |
| 1 | 19 | 56 | 32 | 37 | 79 |
| 2 | 27 | 72 | 49 | 42 | 92 |
| 3 | 35 | 93 | 74 | 52 | 102 |
| 4 | 43 | 95 | 87 | 56 | 103 |
| 6 | 56 | 96 | 97 | 70 | |
| 8 | 68 | 97 | 98 | 81 | |
| 10 | 79 | 97 | 98 | 90 | |
| 12 | 102 | 99 | 100 | 94 | |

Example 3

The following describes a study conducted to determine various pharmacokinetic parameters after administration of a formulation of the present invention and a comparative, commercially available formulation in healthy adult human subjects under fasting conditions.

Figure 2:
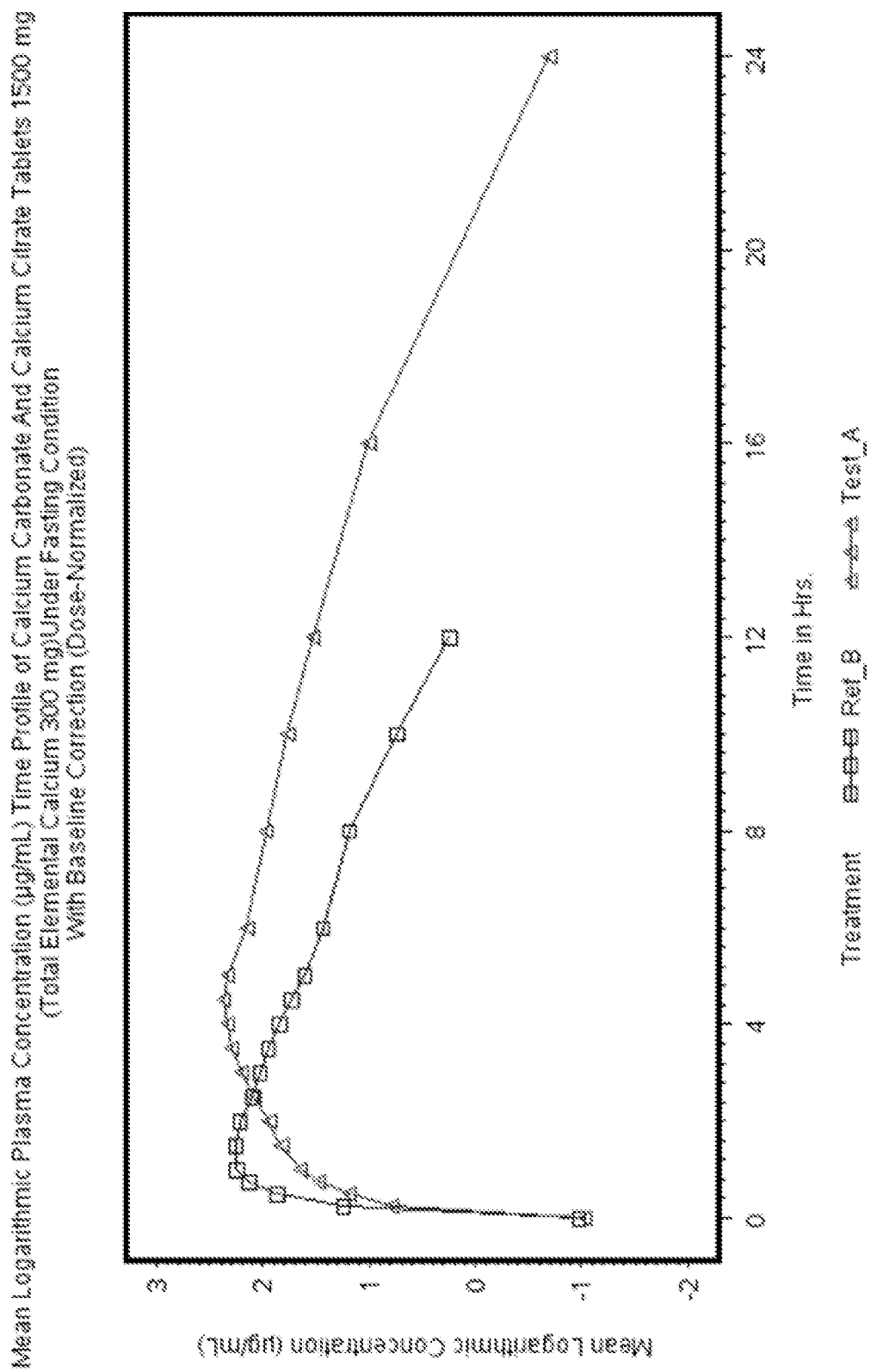
FIG. 2 shows the mean logarithmic plasma concentration time profile (dose-normalized graph) relating to the experiment described in Example 3.

A total of 18, healthy adult human subjects were enrolled in the study. The study had an open label, randomized, two period, two treatment, two sequence, two way crossover design. The subjects were randomly assigned to receive the Test Product (Formulation 4 in Example 2, which is an extended release tablet containing 300 mg of elemental calcium) and the Reference Product (SHELCAL 250 tablets, marketed by Elder Pharmaceuticals Pvt. Ltd., which is an immediate release tablet containing 250 mg calcium carbonate). The subjects received a single oral dose of Test Product or Reference product with 240 mL of water in each study period, with a 7 day wash out period in between each study period. Plasma samples were obtained from subjects before the study and at t=0.25 h, 0.50 h, 0.75 h, 1.0 h, 1.5 h, 2.0 h, 2.5 h, 3.0 h, 3.50 h, 4.00 h, 4.50 h, 5.00 h, 6.00 h, 8.00 h, 10.00 h, 12.00 h, 16.00 h, and 24.00 h post dose. The samples were analyzed and plasma concentrations of calcium were measured. Analysis of variance (ANOVA) was performed ($\alpha=0.05$) on the log-transformed pharmacokinetic parameters of $C_{max}$, $AUC_{0-t}$, $AUC_{0-inf}$. Table 2 shows the dose-normalized results. FIG. 1 shows the mean plasma concentration time profile (dose-normalized graph), and FIG. 2 shows the mean logarithmic plasma concentration time profile (dose-normalized graph).

TABLE 2

| Calcium | TEST PRODUCT (A) | REFERENCE PRODUCT (B) | % Ratio (A/B * 100) |
|---|---|---|---|
| Mean $C_{max}$ (μg/mL) | 11.50 | 10.99 | 106.62 |
| $AUC_{0-t}$ (μg · hr/mL) | 124.56 | 85.56 | 240.99 |
| $AUC_{0-inf}$ (μg · hr/mL) | 170.90 | 124.17 | 266.01 |

The study shows that the Test Product demonstrated a higher $C_{max}$, $AUC_{0-t}$, and $AUC_{0-inf}$ compared to the Reference Product. The AUC was significantly larger after administration of the Test Product, compared to the Reference Product. This observation indicates that absorption of calcium from the gastrointestinal tract is greater with the Test Product.

What is claimed:

1. An orally administrable pharmaceutical composition consisting of:
   (i) a first portion consisting of calcium carbonate, calcium citrate, and one or more pharmaceutically acceptable excipients; and
   (ii) a second portion consisting of calcium citrate as the sole calcium compound and one or more pharmaceutically acceptable excipients;
   wherein the first portion is formulated for immediate release and the second portion is formulated for extended release, and the first portion and the second portion form a layered tablet, and
   wherein the second portion comprises about 50% to 75% of the total amount of calcium compounds in the composition.

2. The orally administrable pharmaceutical composition of claim 1, wherein the first portion is not in direct physical contact with the second portion.

3. The orally administrable pharmaceutical composition of claim 1, wherein the first portion is in direct physical contact with the second portion.

4. The orally administrable pharmaceutical composition of claim 1, wherein about 25% to 75% of the surface area of the first portion is in direct physical contact with the second portion.

5. The orally administrable pharmaceutical composition of claim 1, wherein the layered tablet is a bilayer tablet.

6. The orally administrable composition of claim 1, wherein the first portion comprises about 200 mg to 300 mg of calcium carbonate and about 200 mg to 300 mg of calcium citrate.

7. The orally administrable composition of claim 1, wherein the second portion comprises about 700 mg to 800 mg of the calcium citrate.

8. The orally administrable composition of claim 1, wherein the first portion comprises about 250 mg of calcium carbonate and about 350 mg of calcium citrate, and the second portion comprises about 750 mg of calcium citrate.

9. The orally administrable composition of claim 1, wherein about 25% or more of the total amount of calcium compound(s) is released in the upper gastrointestinal tract.

10. The orally administrable composition of claim 1, wherein about 50% or more of the total amount of calcium compound(s) is released in the upper gastrointestinal tract.

11. A method of treating or reducing the symptoms associated with a medical condition, comprising administering to a subject in need thereof the orally administrable pharmaceutical composition of claim 1, wherein the medical condition is selected from the group consisting of calcium deficiency, osteoporosis and osteopenia.

* * * * *